(12) United States Patent
Franceschini et al.

(10) Patent No.: US 8,915,852 B2
(45) Date of Patent: Dec. 23, 2014

(54) SYSTEM AND METHOD FOR ULTRASOUND SCATTERER CHARACTERIZATION

(71) Applicant: Centre Hospitalier de l'Universite de Montreal, Montreal (CA)

(72) Inventors: Emilie Franceschini, Marseilles (FR); Guy Cloutier, Le Gardeur (CA)

(73) Assignees: Centre Hospitalier de l'Universite de Montreal (CA); Centre National de la Recherche Scientifique (FR)

( * ) Notice: Subject to any disclaimer, the term of this patent is extended or adjusted under 35 U.S.C. 154(b) by 0 days.

(21) Appl. No.: 13/936,689

(22) Filed: Jul. 8, 2013

(65) Prior Publication Data

US 2014/0016438 A1    Jan. 16, 2014

Related U.S. Application Data

(60) Provisional application No. 61/668,710, filed on Jul. 6, 2012.

(51) Int. Cl.
| | |
|---|---|
| *G01S 15/02* | (2006.01) |
| *A61B 8/08* | (2006.01) |
| *G01S 7/52* | (2006.01) |
| *A61B 5/145* | (2006.01) |

(52) U.S. Cl.
CPC ............. *G01S 15/02* (2013.01); *G01S 7/52036* (2013.01); *A61B 5/14535* (2013.01); *A61B 8/5223* (2013.01); *A61B 8/0833* (2013.01)
USPC ................................ 600/437; 367/73; 367/87

(58) Field of Classification Search
CPC ........................................................ A61B 8/083
USPC ........................................ 600/437; 367/73, 87
See application file for complete search history.

(56) References Cited

U.S. PATENT DOCUMENTS

| | | | | |
|---|---|---|---|---|
| 4,265,126 | A | * | 5/1981 | Papadofrangakis et al. ........................ 73/861.25 |
| 4,817,016 | A | * | 3/1989 | Thompson et al. ............. 702/39 |
| 5,243,987 | A | * | 9/1993 | Shiba ............................ 600/463 |
| 5,348,015 | A | * | 9/1994 | Moehring et al. ............. 600/453 |
| 5,588,032 | A | * | 12/1996 | Johnson et al. .................... 378/8 |
| 6,200,266 | B1 | * | 3/2001 | Shokrollahi et al. .......... 600/438 |
| 2002/0102023 | A1 | * | 8/2002 | Yamauchi ..................... 382/199 |
| 2004/0054283 | A1 | * | 3/2004 | Corey et al. ................... 600/438 |
| 2004/0161141 | A1 | * | 8/2004 | Dewaele ....................... 382/132 |
| 2005/0101846 | A1 | * | 5/2005 | Fine et al. ..................... 600/316 |

OTHER PUBLICATIONS

Victor C. Anderson "Sound Scattering from a Fluid Sphere", The Journal of the Acoustical Society of America, Jul. 1950, vol. 22, No. 4, pp. 426-431.

(Continued)

*Primary Examiner* — Luke Ratcliffe
*Assistant Examiner* — Hovhannes Baghdasaryan
(74) *Attorney, Agent, or Firm* — Cantor Colburn LLP

(57) ABSTRACT

A method for characterizing ultrasound scatterers in a medium comprises receiving ultrasound data representing a region of interest comprising a plurality of scatterers in a medium, the plurality of scatterers including aggregates of the scatterers. The ultrasound data is modeled data using an effective medium theory combined with the structure factor model, the structure factor model defining the spatial organization and concentration of the aggregates. The modeled ultrasound data is compared to theoretical data obtained with the effective medium theory combined with the structure factor model. From the comparison, dimensional data of the aggregates of the scatterers and the volume concentration of scatterers in the medium is determined.

3 Claims, 8 Drawing Sheets

Reality                Effective medium approximation

(56) References Cited

OTHER PUBLICATIONS

R. J. Baxter, "Percus-Yevick Equation for Hard Spheres with Surface Adhesion", The Journal of Chemical Physics, Sep. 15, 1968, vol. 49, No. 6, pp. 2770-2774.

R. D. Doolittle et al. "Sound Scattering by Elastic Cylindrical Shells", The Journal of the Acoustical Society of America, Sep. 13, 1965, vol. 39, No. 2, 272-275.

Isabelle Fontaine et al. "Simulation of Ultrasound Backscattering by Red Cell Aggregates: Effect of Shear Rate and Anisotropy"; Biophysical Journal; Apr. 2002; vol. 82, pp. 1696-1710.

Guy T. Kuster, et al. "Velocity and Attenuation of Seismic Waves in Two-Phase Media: Part I. Theoretical Formulations", http://library.seg.org, Oct. 1974, vol. 39, No. 5, pp. 587-606.

Ratan K. Saha et al. "Assessment of accuracy of the structure-factor-size estimator method in determining red blood cell aggregate size from ultrasound spectrum backscattering coefficient", The Journal of the Acoustical Society of America, 2011, vol. 129, No. 4, pp. 2269-2277.

David Savery et al. "A point process approach to assess the frequency dependence of ultrasound backscattering by aggregating red blood cells", The Journal of the Acoustical Society of America, Dec. 2001, vol. 110, No. 6, pp. 3252-3262.

M.S. Wertheim "Exact Solution of the Percus-Yevick Integral Equation for Hard Spheres", Physical Review Letters, Apr. 15, 1963, vol. 10, No. 8, pp. 321-323.

Francois T.H. Yu et al. "Experimental ultrasound characterization of red blood cell aggregation using the structure factor size estimator", The Journal of the Acoustical Society of America, Jul. 2007, vol. 122, No. 1, pp. 645-656.

Francois T.H. Yu et al. "Ultrasonic parametric imaging of erythrocyte aggregation using the structure factor size estimator", Biorheology, 2009, vol. 46, pp. 343-363.

\* cited by examiner

SYSTEM AND METHOD FOR ULTRASOUND SCATTERER CHARACTERIZATION

CROSS-REFERENCE TO RELATED APPLICATIONS

The present application claims priority to U.S. Provisional Application No. 61/668,710, filed on Jul. 6, 2012, incorporated herein by reference in its entirety.

FIELD OF THE INVENTION

The present application relates to ultrasound scatterer characterization, and more particularly to a method and a device for calculating physical parameters of aggregates in a medium, such as red blood cell aggregates in blood.

BACKGROUND OF THE INVENTION

Ultrasound technology is commonly used as part of diagnostic or inspection tools in a range of industries including medicine, foodstuffs, pharmaceuticals, petrochemicals, chemicals and materials processing. Such tools produce characterization of data in a non-invasive or non-destructive fashion. In known ultrasound methods, ultrasounds are transmitted to scatterers in a medium and backscattered or scattered echoes are detected. Ultrasound parameters such as backscattering coefficient, angular scattering, attenuation, speed of sound, material nonlinearity and statistics can then be used to reveal intrinsic material properties of the scatterers or the medium such as microstructure and/or composition.

In ultrasound imaging of biological tissues, the ultrasound signal backscattered by the components of the tissue has been used to extract quantitative properties of the scatterers to reveal properties such as the correlation length of structures composing the medium. This method and the other aforementioned approaches have been used successfully to detect and diagnose medical conditions, such as prostate cancer, early Duchenne muscular dystrophy, cell apoptosis and carcinomas.

However, these methods are not suitable for all applications. They are particularly unsuitable for characterizing dense concentrations of scatterers in a medium such as dense suspensions of particles or cells. It is desirable to obtain quantitative information regarding the physical dimensions of such scatterers. For example, in two-phase systems such as solid particles/droplets of insoluble liquid/gas bubbles in a fluid, it is desirable to quantitatively characterize the suspensions in terms of the suspended particle size, concentration and other physical parameters.

One such application is in medical diagnostics where the aggregation of red blood cells is known to be an independent risk factor of circulatory related disorders such as thrombosis, atherosclerosis and valvular heart disease. Red blood cell aggregation is also a surrogate marker of inflammation. Furthermore, the presence and size of circulating embolisms in the blood vessels of a patient can be indicative of their risk of suffering a stroke or a coronary artery ischemic syndrome.

For years, many investigators have attempted to quantify the ultrasound backscatter from blood by analyzing the power spectra of the radio frequency (rf) echoes to estimate the aggregation level of red blood cells (RBCs). The aim is to detect abnormal RBC aggregation and its pathophysiological impact on associated circulatory diseases, namely, deep venous thrombosis, atherosclerosis, and microcirculatory flow disorders such as in diabetes mellitus. The hypothesis is that ultrasound blood characterization techniques can provide in vivo and in situ evaluation of RBC aggregation for diagnostic purposes.

Two quantitative ultrasonic parameters that have been proven useful for blood characterization are the backscattering coefficient (BSC) and the spectral slope (SS). The BSC is defined as the differential backscattering cross section per unit volume and the SS is the linear slope of the BSC as a function of frequency on a log-log scale. In most numerical and in vitro experimental studies, the BSC increases and the SS decreases as the level of aggregation increases.

Ultrasound backscattering by blood is mainly due to RBCs that constitute a major portion of the blood cellular content. Blood can thus be described as a biphasic fluid composed of RBCs immersed in plasma at a volume concentration (i.e., a systemic hematocrit) typically varying between 30 and 50%. The high cellular number density of blood induces destructive wave interferences and a nonlinear backscattered power versus hematocrit relationship.

In the absence of aggregation, a few stochastic scattering models were proposed to better understand the ultrasound backscattered power properties. Two classical approaches are known as the particle and continuum models. The particle model (PM) consists of summing contributions from individual RBCs, all considered much smaller than the acoustic wavelength, and modeling the RBC interaction by an analytical packing factor expression. The continuum model (CM) considers that scattering arises from spatial fluctuations in the density and compressibility of the blood continuum. In a hybrid model generalizing the PM and CM frameworks, the RBCs are treated as a single scattering unit within a voxel, which size is defined as a fraction of the acoustic wavelength. The contribution from each single scattering unit is then determined as in the PM, and the contribution from all voxels is then summed by considering the influence of the mean number of scatterers per voxel and its variation in numbers between voxels. The framework of the hybrid model was generalized and the structure factor model (SFM) was introduced for the case of non-aggregating RBCs.

A major difficulty for modeling blood backscattering is to consider clustering particles as RBC aggregates. The aforementioned approaches are valid in the Rayleigh scattering regime (i.e., for a product of the wavenumber k times the scatterer radius a, ka<<1), which is characterized by a fourth-order frequency dependence (spectral slope SS=4), whereas the SS for aggregated RBCs differs from the fourth power law. Accordingly, Savery and Cloutier ("*A point process approach to assess the frequency dependence of ultrasound backscattering by aggregating red blood cells*," J. Acoust. Soc. Am., vol. 110, No. 6, pp. 3252-3262, 2001) proposed the SFM to predict backscattering by aggregating RBCs at a low hematocrit. This model was later generalized to a normal hematocrit of 40% (Fontaine, Savery and Cloutier, "Simulation of ultrasound backscattering by red blood cell aggregates: effect of shear rate and anisotropy", Biophysical Journal, vol. 82, pp. 1696-1710, 2002). The SFM sums the contributions from individual RBCs and models the RBC interaction by a statistical mechanics structure factor, which is by definition the Fourier transform of the spatial distribution of RBCs. It is important to emphasize that the low frequency limit of the structure factor is by definition the packing factor used under Rayleigh scattering conditions, and that the structure factor cannot analytically be calculated contrary to the packing factor. To estimate the aggregate structure parameters by fitting the measured BSC to a modeled BSC, the SFM would be computationally intensive because of the various possible RBC spatial distributions that would need to be estimated for statistical robustness, under both normal and pathological aggregating conditions. Yu et al. ("*Experimental ultrasound characterization of red blood cell aggregation using the structure factor size estimator,*" J. Acoust. Soc. Am., vol. 122, No. 1, pp. 645-656, 2007; "*Ultrasonic parametric imaging of erythrocyte aggregation using the structure factor size estimator,*" Biorheology, vol. 46, pp. 343363, 2009) recently developed a scattering theory, called the structure factor size estimator (SFSE), that approximates the SFM by using a second-order Taylor expansion of the structure factor. The SFSE parameterizes the BSC by two structure indices: the packing factor and mean aggregate diameter assumed to be isotropic. However, experiments with pig blood in controlled flow devices and three-dimensional numerical simulations of isotropic aggregates showed that the two indices may follow a quadratic relationship, reducing the BSC parameterization to one parameter.

With current existing SFSE technology, one can acquire ultrasound RF data from a blood vessel, estimate the backscatter coefficient BSC over the frequency bandwidth of acquired data, fit a BSC model as a function of frequency to the experimental BSC data, and estimate the packing factor and mean aggregate size. With such state-of-the-art, one can obtain parametric cellular images of RBCs and RBC aggregates flowing within blood vessels. Those images can then be used for the abovementioned applications, for example the diagnosis of blood circulatory disorders and quantification of the inflammatory response of a disease. None of these prior art techniques allows the measure of the compactness of the RBC aggregates. Also, the bias resulting from the use of these methods needs to be reduced in order to provide a more accurate characterization of the RBC aggregates. There is therefore a need for a new imaging method providing additional physical parameters describing the structure of flowing RBC aggregates with better accuracy than the above mentioned methods.

BRIEF SUMMARY OF THE INVENTION

It is therefore an aim of the present invention to provide a method and system for ultrasound scatterer characterization.

It is a further aim of the present disclosure to provide a method and system to determine at least one of a dimensional value of aggregates of scatterers, a concentration of scatterers within aggregates, and a volume concentration of scatterers.

Therefore, in accordance with the present application, there is provided a method for characterizing ultrasound scatterers in a medium, the method comprising: receiving ultrasound data representing a region of interest comprising a plurality of scatterers in a medium, the plurality of scatterers including aggregates of the scatterers; modeling the ultrasound data using an effective medium theory combined with the structure factor model (i.e., a theory considering the ultrasound insonified tissue as a continuum embedding spatially organized particles), the effective medium theory considering that the aggregates are individual homogeneous scatterers and the structure factor model defining the spatial organization and concentration of the aggregates; comparing the modeled ultrasound data to theoretical data obtained with the effective medium theory combined with the structure factor model; and determining from the comparison dimensional data of the aggregates of the scatterers (such as the size and compactness of aggregates) and the volume concentration of scatterers in the medium. The main advantage of the method is the consideration of the compactness of aggregates.

Further in accordance with the present disclosure, there is provided a system for characterizing ultrasound scatterers in a medium, the system comprising: a transmitter for transmitting an ultrasound signal to a region of interest, the region of interest comprising a plurality of scatterers in a medium including aggregates of the scatterers; at least one detector for detecting a scattered or a backscattered ultrasound signal; and a processor for converting the detected ultrasound signal to ultrasound data representing the region of interest, for modeling the ultrasound data using an effective medium theory combined with the structure factor model, the structure factor model defining the spatial organization and concentration of the aggregates; comparing the modeled ultrasound data to theoretical data obtained with the effective medium theory combined with the structure factor model; and determining from the comparison dimensional data of the aggregates of the scatterers (such as the size and compactness of aggregates) and the volume concentration of scatterers in the medium.

DETAILED DESCRIPTION OF THE INVENTION

Figure 1:
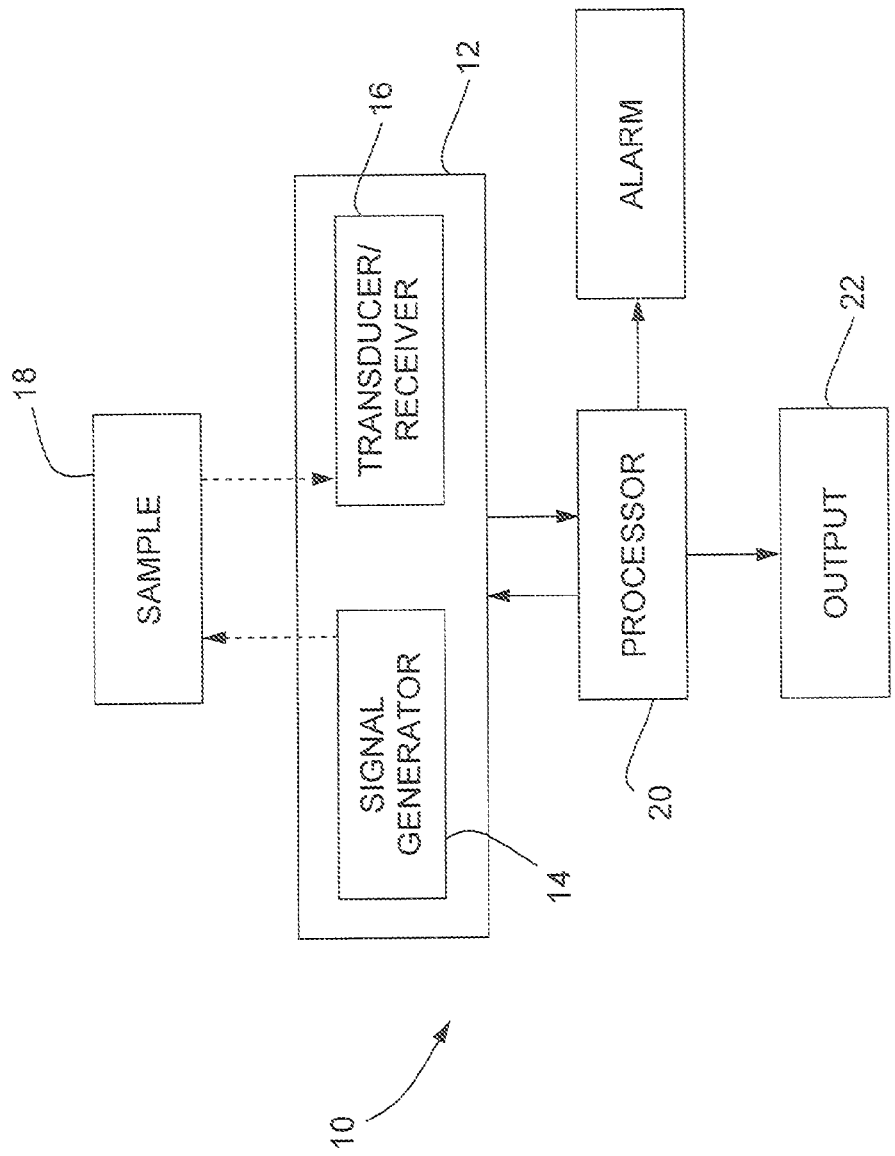
FIG. 1 is a block diagram of a system for ultrasound scatterer characterization in accordance with an embodiment of the present disclosure.

Referring to the drawings and more particularly to FIG. 1, a system 10 for characterizing ultrasound scatterers, according to an embodiment of the present disclosure, is described below. The system 10 may be used to characterize aggregates in a medium, and is particularly suited to characterize red blood cell aggregation in blood. Accordingly, the present disclosure will refer to the characterization of red blood cell aggregation, although the system 10 and method could be used in other applications.

The system 10 comprises a probe unit 12 or several probes at different frequencies for transmitting an ultrasound signal typically between 1 MHz to 1 GHz to a region of interest and for detecting a backscattered ultrasound signal. Specifically, in blood characterization, the region of interest comprises a plurality of aggregates of red blood cells (RBCs) suspended in blood plasma, the aggregates having physical property values to be estimated. The physical properties of the RBCs are estimated by backscattered ultrasound signals. Specifically, these are the aggregate radius or like dimension value in number of RBCs or equivalent dimensional measure in micrometers, the internal hematocrit (i.e., the concentration of RBCs in the aggregates, which may typically vary from 100%—no aggregation—to 10%—loose aggregates), the hematocrit (i.e., the volume fraction of RBCs in blood, which is normally above 20%—to avoid blood transfusion due to severe anemia—and below typically 60%—as found in individuals living at high altitude), and the fraction of aggregated RBCs in blood (which depends on the abovementioned physical parameters). However, the system 10 and the method described hereinafter may be applied to any other cells in blood as well as to any other suspensions and emulsions other than blood, and to scatterers in a solid medium.

The system 10 is schematically shown in FIG. 1. The transmitter and detector comprise a signal generator 14 or pulser and a transducer/receiver 16. The signal generator 14 and the transducer/receiver 16 may be incorporated in a single casing of the probe unit 12. The signal generator 14 generates an electrical signal which is transmitted to a transducer 16. The transducer 16 converts the electric signal into an acoustic input signal that is introduced into a sample 18. The transducer/receiver 16 acts as a sensor to sense or detect at least a portion of the acoustic energy that is backscattered by the sample in response to its interaction with the acoustic input signal. Therefore, the transducer/receiver 16 provides an output signal to the processor 20. The processor 20 processes the output signal to provide an output 22 (e.g., monitor, display screen, alarm, etc) which is at least one dimension value of aggregates of the scatterers, and a volume concentration of the scatterers in the medium. The processor 20 is programmed to operate according to a proposed method described hereinafter, to produce a dimension value (e.g. aggregate radius) of the aggregates of RBCs, as well as an internal hematocrit value of the aggregates and the fraction of aggregated RBCs in blood, in addition to the hematocrit of the blood sample 18 (i.e., the volume fraction of RBCs in blood).

Alternatively, the system 10 may include one or several separate transducers/probes as a receiver or receivers (shown as transducer/receiver 16). In this case, one transducer transmits echoes and the other receives echoes. Alternatively, several transducers can be used as transmitters and receivers to cover a large frequency bandwidth.

In the blood characterization embodiment, the sample 18 comprises individual RBCs and/or aggregates of RBCs in blood plasma. As the present embodiment of the system 10 relates to an in vivo estimation of physical parameters of clustered RBCs, the sample 18 is a blood vessel of a patient which can be considered as a 'live' vessel. In an embodiment, the transducer/receiver 16 is positioned on the skin of the patient over a blood vessel lying underneath the skin. This can provide real-time information on the red blood cell aggregation of the patient. In an alternative embodiment, the system 10 and the related method of the invention can be applied to obtain an in vitro physical parameter estimation. In the in vitro case, a blood sample is taken from a patient and the transducer 16 is positioned in the blood sample or on a wall of a container containing the sample and the sample agitated to avoid sedimentation. One of the characteristic of the above-mentioned container being its compatibility with ultrasound (i.e., low attenuation and low impedance mismatch between the wall of the container and the sample within it), in the case of measurements through the wall of the container. It will be appreciated that the sample can therefore be in any form in which an ultrasound signal can be transmitted to aggregates in the sample.

Considering now the individual components of FIG. 1, for illustrative purposes and non-limitatively, the signal generator 14 may be a monocycle generator capable of producing a single cycle of radio-frequency signals at pre-settable pulse frequencies, or any other suitable signal generator. For measuring RBCs in blood, the frequency is set within the range of 1 MHz to 1000 MHz typically and a pulse repetition rate between 500 Hz and 5 kHz is used. A commercially available monocycle generator can be used such as Avtech pulse generator (model AVB2-TA-C-CRIMA, Ottawa, Canada), if one considers limiting frequencies between 10 and 80 MHz, typically.

The transducer 16 can be any type of broadband ultrasound transducers such as those used with the Vevo 770 ultrasound scanner (VisualSonics, Toronto, Canada). In this embodiment, the Vevo 770 single-element focused circular transducer may have a center frequency of 25 MHz, a transducer diameter of 7.1 mm and a focal depth of 15 mm is used to acquire and store radio-frequency lines. The transducer 16 includes a receiver portion which receives the backscattered ultrasound signals and transmits them to the signal processor 20.

For detecting red blood cells in blood, the transducer 16 may have a centre frequency of 25 MHz, and preferably be within the range of 10-40 MHz. The operating frequency is chosen as a function of the measurement contemplated. Therefore, in alternative embodiments where the system 10 and the proposed method 12 are applied to other particle suspensions or weak scatterers in a homogenous medium, transducers with a lower or a higher frequency range can be used, for example transducers having frequencies below 1 MHz and above 100 MHz up to 1000 MHz (or 1 GHz). Multiple transducers can also be used. The relationship between frequency, relative wavelength and scatterer size (ka) is known and appropriate frequencies can be selected on this basis.

The processor 20 may include an amplifier for amplifying the signal and a converter for converting the analogue signal to a digital signal. In this embodiment, commercially available diplexers, amplifiers and converters are used such as Ritec diplexer (model RDX-6, Warwick, R.I., USA), a 10 dB Mitec linear amplifier (model AU-A3-0120, Hauppauge, N.Y., USA), and an 8-bits 500 MHz sampling frequency GageScope acquisition board (model 8500CS, Montreal, Canada).

Further processing of the digital signal is either performed by the processor 20, or another processor (not shown) such as a computer or any other digital signal processor. The further processing may include normalizing the digital signal, and conversion of the digital signal to ultrasound data representing a power spectrum, in addition to the application of the embodiment of the method of the present disclosure, to estimate aggregate size, internal aggregate packing, hematocrit and/or area fraction. The processor 20 may also include a memory for storing the digital signal, storing instructions for the data processing, and storing the output data 22 of the data processing. The system 10 may include an interface 24 for displaying the output data 22, the power spectrum or the digital signal, and for the manual entry of data by the user.

The processor 20 may include an oscilloscope which converts the ultrasound digital signal and displays the processed output signal (e.g. as a power spectrum), linked to a further processor for estimating the physical parameter values of the red blood cell clusters.

The system 10 may be contained within a single housing to form a single apparatus or portable device comprising separate parts. Single housing embodiments may be suitable for in situ and in vivo uses, bedside or self-monitoring applications, for example. Such an apparatus may also be applied to in vitro particle characterization methods for applications where sampling is preferable.

Also, the system 10 may comprise an alarm or alert device coupled to the processor 20 for indicating if and when the estimated physical parameters match, come close to, fall below or exceed a pre-defined threshold limits or ranges. For example, in the case of red blood cell aggregation, the alarm can be activated automatically if the detected aggregated size comes close to, reaches or exceeds a predefined dangerous aggregate size. This in turn may activate an automatic administration of drugs or other therapy or treatment.

Now that the system 10 has been described, a method for characterizing blood in accordance with the present disclosure is set forth. The method of the present disclosure is performed by the processor 20 of the system 10, or by any other processor receiving output data from ultrasound scanning on the output 22.

The method of the present disclosure is based on the Effective Medium Theory combined with the Structure Factor Model (EMTSFM), hereinafter referred to as "the method of the present disclosure," applied to the frequency-dependent backscattering coefficient (BSC) of blood. In the blood characterization embodiment, physical parameters are extracted from the model and experimental ultrasound (US) measures of BSC to describe the level of aggregation, a marker of inflammation: the aggregate radius, the internal hematocrit (i.e., the concentration of RBCs within aggregates, which is affected by the binding energy between aggregates, also known as the aggregate strength) and the hematocrit (i.e., the fraction of aggregated RBCs in blood). These parameters may be used to provide a real-time monitoring, in surgery rooms and emergency or intensive-care units, of the level of inflammation by measuring the characteristics of RBC aggregates with US; an alarm to indicate abnormally high levels of aggregation to support medical decisions; and a stand-alone dedicated instrument for in-bed critical patient monitoring, as it is currently done for physiological measures such as the electrocardiogram, blood pressure, body temperature, respiration rate and systemic oxygen saturation with pulse oxymetry. The method is non-invasive, non toxic and quantitative.

In the following, the present disclosure refers to clustering characteristics of RBCs and corresponding modeling in the framework of the EMTSFM cellular imaging method. Firstly, there is described a condition where all aggregates of RBCs have statistically the same mean dimension, whereas there is secondly described a case where RBC structures may have different mean dimensions within a given region-of-interest (i.e., aggregates of similar mean sizes mixed with individual RBCs forming no aggregation). These two conditions represent a subset of possible clustering conditions provided non-limitatively to show the reliability of the proposed EMTSFM method. This is followed by validations with simulations and experiments of proposed modeling with the EMTSFM parametric method to provide images of RBC physical characteristics. In practice, the use of the present disclosure does not necessitate simulations, as a processing step.

Monodisperse Model

Figure 2:
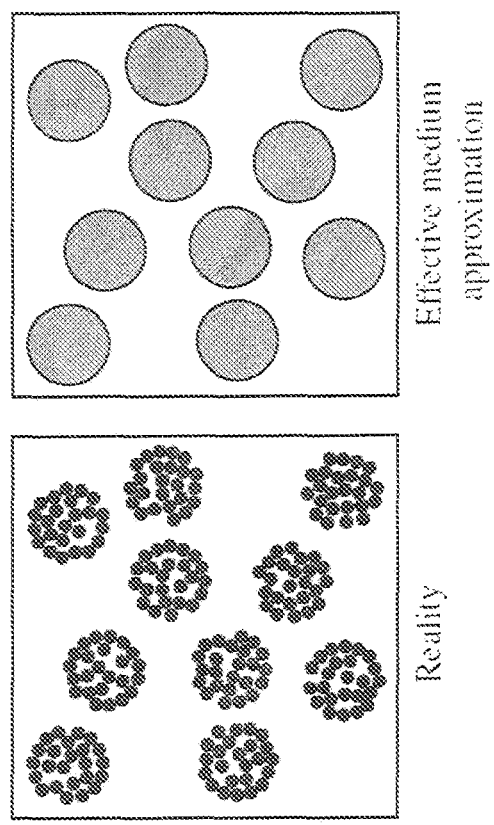
FIG. 2 is a schematic view of aggregates of scatterers as treated as individual homogeneous scatterers.

As a first approximation, it is assumed that all the scatterers (RBCs in an embodiment) are aggregated, that the aggregates are identical and isotropic and that the RBCs within the aggregates are evenly distributed. The method of the present disclosure assumes that aggregates of RBCs can be treated as individual homogeneous scatterers as shown in FIG. 2. Each aggregate is thus approximated by an effective single sphere having a radius $r_{ag}$. The density $\rho_{ag}$ and compressibility $\kappa_{ag}$ of the new effective sphere can be determined by considering the effective medium theory developed by Kuster and Toksoz ("*Velocity and attenuation of seismic waves in two-phase media: part I. Theoretical formulations,*" Geophysics, vol. 39, No. 5, pp. 587-606, 1974), in addition to the data of Table I.

TABLE I

| | Density $\rho$ (kg · m$^{-3}$) | Compressibility $\kappa$ (Pa$^{-1}$) | Impedance Z (MRayl) |
|---|---|---|---|
| RBC | 1092 | 3.41 × 10$^{-10}$ | 1.766 |
| Plasma | 1021 | 4.09 × 10$^{-10}$ | 1.580 |

Consequently, $\rho_{ag}$ and $\kappa_{ag}$ are derived from the acoustical properties of the two fluids that constitute the aggregates (i.e., $\rho_1, \rho_2, \kappa_1$ and $\kappa_2$, where 1 indicates properties of RBCs and 2 those of plasma) and from the internal concentration of RBCs within the aggregates, defined as the internal hematocrit $\phi_i$, as follows:

$$\rho_{ag} = \phi_i \rho_1 + (1-\phi_i)\rho_2 \qquad (1)$$
$$\frac{1}{\kappa_{ag}} = \frac{\phi_i}{\kappa_1} + \frac{1-\phi_1}{\kappa_2}.$$

The acoustic interaction of RBCs within aggregates is therefore taken into account in the method of the present disclosure, similarly to the SFM where it is considered by the structure factor that models the individual position of RBCs and their acoustical interaction whether they are within an aggregate or not. An advantage of the method of the present disclosure is the consideration of the compactness of aggregates with the parameter $\phi_i$.

The BSC from blood is then obtained by summing contributions from individual effective particles of radius $r_{ag}$ and modeling the effective particle interaction by a statistical mechanics structure factor $S_{ag}$. The equivalent BSC expression is thus given by:

$$BSC_{eq}(-2k) = m_{ag}\sigma_{ag}(-2k)S_{ag}(-2k), \qquad (2)$$

where $m_{ag}$ is the number density of aggregates that is related to the effective volume fraction of aggregates $\phi_{ag}$. The effective volume fraction of aggregates is equal to the volume fraction of RBCs in blood $\phi$ divided by the internal hematocrit $\phi_i$: $\phi_{ag} = \phi/\phi_i$. The backscattering cross-section $\sigma_{ag}$ of an effective single sphere may be calculated using the fluid-filled sphere model developed by Anderson ("*Sound scattering from a fluid sphere,*" J. Acoust. Soc. Amer., vol. 22, pp. 426-431, 1950) or using an approximated fluid-filled sphere model, or a model considering the real shape of RBC aggregates (not necessarily isotropic and spherical). The model developed by Anderson provides a solution for the backscattering of sound by a single fluid sphere, not necessarily small compared to the wavelength, in a surrounding fluid medium (i.e., the plasma). Using appropriate frequencies, the backscattering cross-section $\sigma_{ag}$ of an effective single sphere may be well approximated by a fluid-filled sphere model given by $$\sigma_{ag}(-2k) = \frac{4k^4 r_{ag}^6 \gamma_{zag}^2}{9}\left(3\frac{\sin(2kr_{ag}) - 2kr_{ag}\cos(2kr_{ag})}{(2kr_{ag})^3}\right)^2 \quad (3)$$

where $z_{ag}$ is the impedance of the equivalent particle and $\gamma_{zag}$ is the relative impedance difference between the equivalent particle and the plasma.

The structure factor $S_{ag}$ dictates how backscattering varies with the spatial organization of effective particles and can be calculated for a collection of identical and effective particles $N_{ag}$ of radius $r_{ag}$ randomly distributed as follows:

$$S_{ag}(-2k) = E\left[\frac{1}{N_{ag}}\left|\sum_{i=1}^{N_{ag}} e^{-i2kr'_i}\right|^2\right] \quad (4)$$

where $r'_i$ are the position vectors defining the center of the $i^{th}$ effective sphere (or aggregate) in space. The structure factor can be analytically calculated for some specific cases. In the case of a random distribution of hard-spheres or sticky hard-spheres in 3D, a solution for the structure factor can be analytically calculated as established by Wertheim (M. S. Wertheim, "Exact solution of the Percus-Yevick integral equation for hard spheres", Physical Review Letters, vol. 10, no. 8, pp. 321-323, 1963) or as established by Baxter (R. J. Baxter, "Percus-Yevick Equation for Hard Spheres with Surface Adhesion", J. Chem. Phys., vol. 49, pp. 2770-2774, 1968 respectively.

It is possible to perform the monodisperse model in a two-dimension approximation as well (as opposed to the three-dimensional model using spheres). The monodisperse model is performed by approximating each aggregate as being an effective single cylinder having a radius $r_{ag}$, with equations (1), (2) and (4). However, the backscattering cross-section $\sigma_{ag}$ of an effective single cylinder can then be calculated using the fluid-filled cylinder model developed by Doolittle and Uberall ("Sound scattering by elastic cylindrical shells", J. Acoust. Soc. Amer., vol. 39, no. 2, pp.272-275, 1965).

Polydisperse Model

In blood, only a fraction of the RBCs are aggregated. In the following, a second embodiment of the present disclosure assumes that a fraction of RBCs $\Phi$ are aggregated, while the rest [i.e., a fraction $(1-\Phi)$] remains disaggregated, and that all the aggregates are identical and isotropic.

The equivalent BSC expression for partially aggregated RBCs denoted $BSC_{eqP}$ can be obtained by a mixing law:

$$BSC_{eqP}(-2k) = \Phi BSC_{eq}(-2k) + (1-\Phi)BSC_{desag}(-2k), \quad (5)$$

where $BSC_{eq}$ is the BSC if all RBCs were aggregated (by considering a volume fraction of RBCs equal to $\Phi\phi$) and $BSC_{desag}$ is the BSC if all the RBCs were disaggregated (by considering a volume fraction of RBCs equal to $(1-\Phi)\phi$). The value of $BSC_{eq}$ can be computed using the proposed EMTSFM method for monodisperse distributions as in equation 2. The value of $BSC_{desag}$ can be computed using the low-frequency limit (i.e., by extrapolating the value of the backscatter coefficient at the frequency of zero Hz) of the Structure Factor Model (see equations 1 and 3 of Yu et al., "Experimental ultrasound characterization of red blood cell aggregation using the structure factor size estimator," J. Acoust. Soc. Am., vol. 122, No. 1, pp. 645-656, 2007).

3D Computer Simulations

In the following, we present simulations aiming at evaluating experimental biases to be obtained if one would consider the case of monodisperse or polydisperse aggregates. They do not represent an embodiment of the present invention. The BSCs computed with the Structure Factor Model (SFM) for several aggregation configurations were used to mimic the response of 3D RBC distributions to an ultrasound excitation. The simulated BSC were obtained from the method described in section III of the article of Saha et al. ("Assessment of accuracy of the structure-factor-size-estimator method in determining red blood cell aggregate size from ultrasound spectrum backscattering coefficient," J. Acoust. Soc. Am., vol. 129, No. 4, pp. 2269-2277, 2011). Random distributions for aggregating RBCs were computed within the simulated volume of $1000 \times 125 \times 125$ µm$^3$. The RBC radius a was set to 2.75 µm for all simulations. We first specified the systemic hematocrit $\phi$, the aggregate radius $r_{ag}$ and the aggregate compactness $\phi_i$ (i.e. the RBC concentration within aggregates). The RBCs were stacked by following a hexagonal close packing (HCP) structure for each aggregate, such that the distribution of RBCs within each aggregate was identical. This HCP structure provides the highest compactness that is about 0.74 for spheres. Aggregates of identical radii $r_{ag}$ and of identical compactness $\phi_i$ were randomly distributed with non-overlapping positions and then a small number of non-aggregated RBCs was added to reach the desired systemic hematocrit.

By assuming that the RBC radius a, the hematocrit $\phi$ and the acoustical properties of plasma and RBCs are known a priori, the unknowns parameters are the radius of aggregates $r_{ag}$ and the internal hematocrit $\phi_i$. The unknown parameters used as "reference values" to compare predictions with the EMTSFM invention were estimated by matching the simulated BSC of the reference SFM model with the theoretical $BSC_{eq}$ given by equation 2. Herein, an analytical expression of the structure factor for a random distribution of hard-spheres from Wertheim (M. S. Wertheim, "Exact solution of the Percus-Yevick integral equation for hard spheres", Physical Review Letters, vol. 10, no. 8, pp. 321-323, 1963) was used. The parameter estimation procedure was done using the minimization routine "fminsearch" in MATLAB (The MathWorks, Inc., Natick, Mass.), i.e. a Nelder-Mead simplex method. It is pointed out that this fit was realized in the frequency bandwidth from 4 MHz to the frequency corresponding to the first minimum of the simulated BSC (i.e., after the frequency-dependent increase in BSC followed by a peak and a reduction to its first minimum).

The following paragraphs present simulation results and corresponding accuracy of the EMTSFM predictions. Concurrently are given results with the SFSE imaging method for comparison purpose only. The SFSE and EMSTFM were examined when the aggregate size varied and the aggregate compactness was fixed to a high value: $\phi i=74\%$. It is important to note that the 3D simulated aggregates were highly packed leaving small numbers of particles as non-aggregated RBCs. For each tissue realization, the actual mean aggregate radius rag was computed using Eq. (6) in Saha et al. ("Assessment of accuracy of the structure-factor-size-estimator method in determining red blood cell aggregate size from ultrasound spectrum backscattering coefficient," J. Acoust. Soc. Am., vol. 129, No. 4, pp. 2269-2277, 2011) and then the concentration of aggregated RBCs $\phi'$ was computed as:

$$\phi' = \frac{\phi_i N_{ag}(4/3)\pi r_{ag}^3}{1000 \times 125 \times 125 \times (10^{-6})^3} \quad (6)$$

Figures 3A, 3B, 3C:
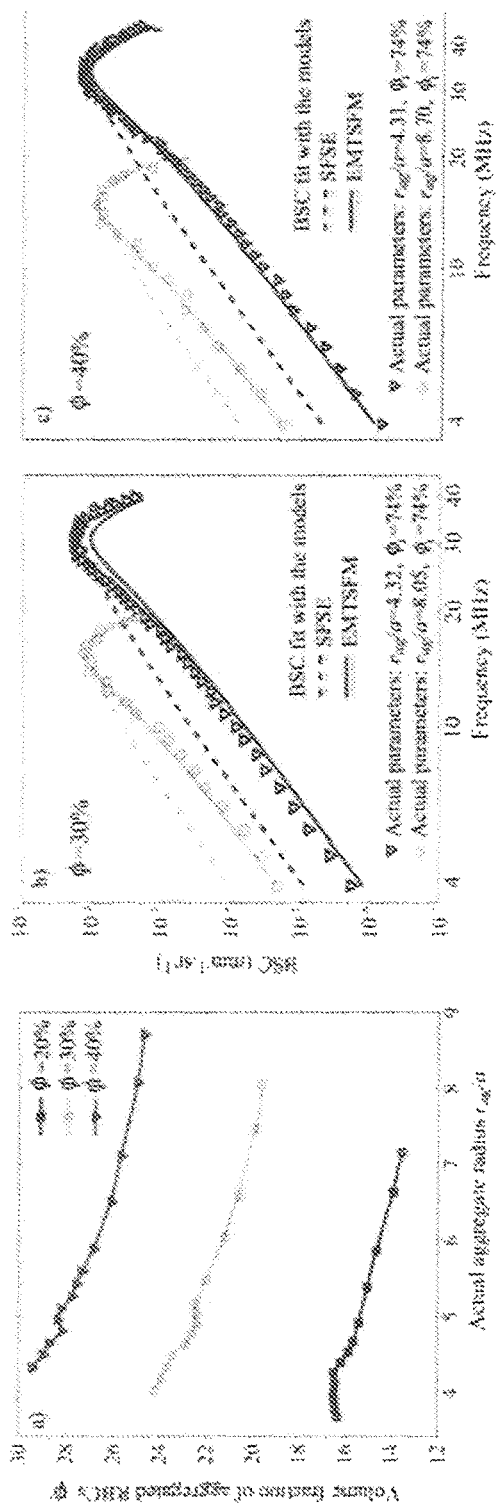
FIG. 3a is a graph showing the concentration of aggregated RBCs as a function of the mean aggregate radius for the three systemic hematocrits of 20, 30 and 40%.
FIGS. 3b and c are graphs showing the frequency-dependent backscattering coefficients computed with the structure factor model for different aggregate sizes and a constant aggregate compactness of 74% at systemic hematocrits of 30 and 40%, and the corresponding fitting with the Structure Factor Size Estimator (SFSE) and the Effective Medium Theory combined with the Structure Factor Model (EMTSFM)

FIG. 3a shows the values of φ' as a function of the mean normalized aggregate radius rag/a for three simulated systemic hematocrits of 20, 30 and 40%. The percentage of disaggregated RBCs was between 20 and 30% for the systemic hematocrit of 20% and between 27 and 37% for the systemic hematocrit of 40% (the latter hematocrit being a condition mimicking the normal hematocrit of a healthy human subject). Note that, for this specific validation, the SFSE and the EMTSFM assumed that all RBCs were aggregated in blood and that aggregates had identical shape and size. Consequently, during the inversion procedure of the 3D BSC data, we neglected the contribution of the disaggregated RBCs on the simulated BSC and we replaced the hematocrit φ by the value of the concentration of aggregated RBCs φ'.

FIGS. 3b and c shows the simulated BSC as a function of frequency for several aggregate sizes and systemic hematocrits of 30 and 40%. Also represented in FIGS. 3b and c are corresponding fitted curves obtained with the SFSE and EMTSFM. The fitted SFSE curves did not produce good fits to the 3D data and overestimated the simulated BSC amplitude (especially in the low frequency range). At the opposite, the EMTSFM provided good fittings to the simulated BSC curves.

Figure 4:
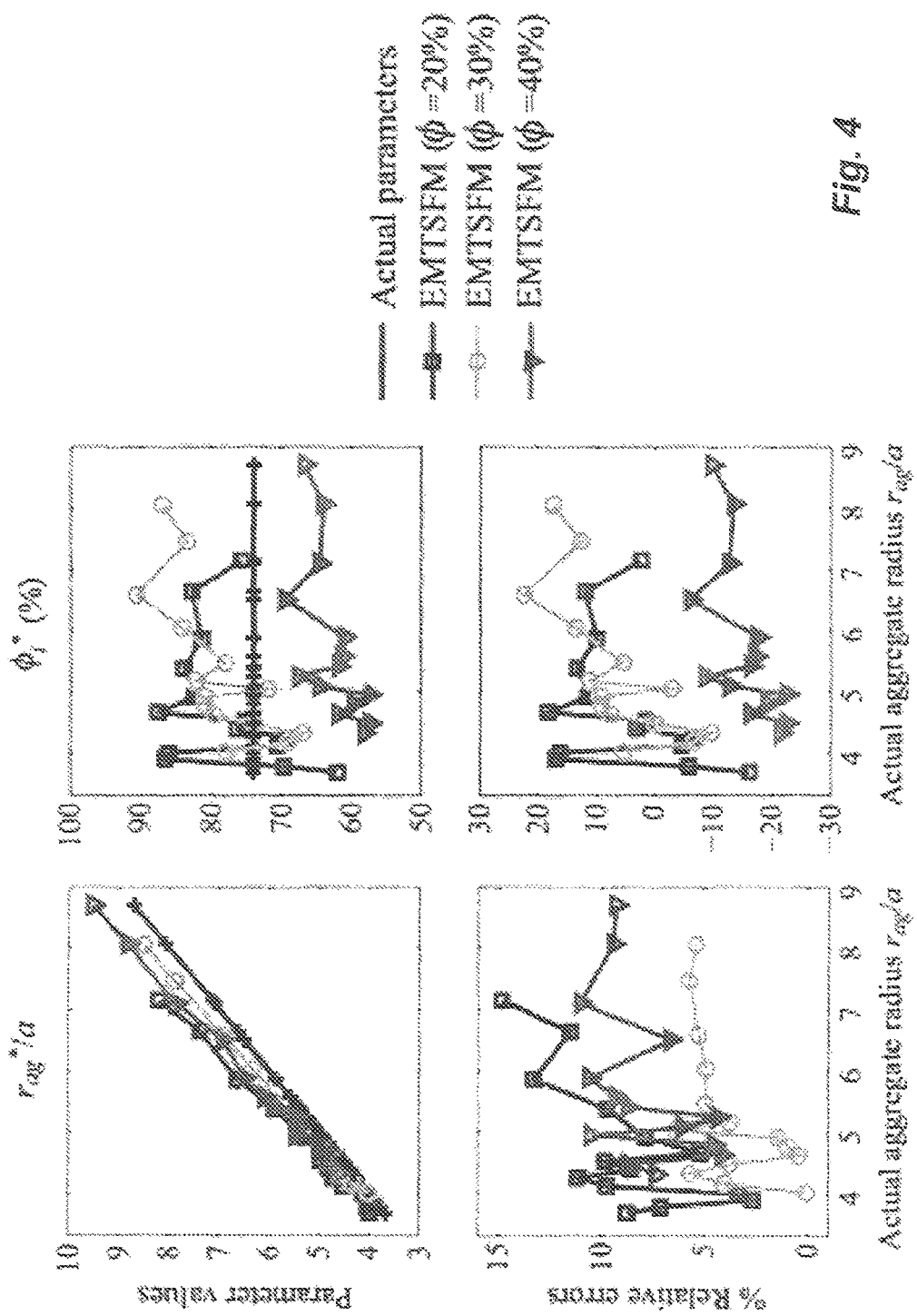
FIG. 4 is a graph showing the values of the aggregate radius $r_{ag}^*/a$, and the aggregate compactness $\phi_i^*$ estimated by the Effective Medium Theory combined with the Structure Factor Model as a function of the actual aggregate radius for the three systemic hematocrit of 20, 30 and 40%, with the corresponding relative errors.

FIG. 4 gives the values of rag* and φi* estimated with the EMTSFM and corresponding relative errors that were less than 15% and 23%, respectively, for all hematocrits. The EMTSFM gave thus quantitatively satisfactory structural parameter estimates. To conclude, the EMTSFM was more suitable than the SFSE for characterizing the aggregate microstructure; it is thus advantageous compared with state-of-the-art technologies. In addition, the EMTSFM provides an estimation of the aggregate compactness, which is not available from any existing ultrasound-based imaging methods.

Experimental Study

An experimental set up was set forth to implement the proposed method and to demonstrate the practical value of the proposed EMTSFM method.

In the experimental set up, fresh porcine whole blood was obtained from a local slaughter house, centrifuged and the plasma and buffy coat were removed. Three blood samples were then prepared: (i) a S6 reference sample, which was a 6% hematocrit non-aggregating RBCs resuspended in saline solution; (ii) a S20 reference sample, which was a 20% hematocrit non-aggregating RBCs resuspended in saline solution; and (iii) a 20% hematocrit T20 test sample, which consisted of RBCs resuspended in plasma to promote aggregation.

All ultrasound measurements were made at room temperature. Prior to each measurement, the T20 blood was sheared at 200 s$^{-1}$ during 30 s to disrupt RBC aggregates. The shear rate was then reduced to residual values of 2, 5, 10 and 50 s$^{-1}$ for 90 s until an equilibrium in the state of aggregation was reached. For each shear rate, 20 B-mode images were constructed from acquired RF echoes each 4 s for a total period of analysis of 80 s. Each image contained 384 vertical lines. For 180 vertical lines at the center of the B-mode images, echoes were selected with a rectangular window of length 0.8 mm at one depth (corresponding to the center of the Couette instrument used for this validation). The power spectra of the back-scattered RF echoes were averaged over 20 acquisitions (corresponding to the 20 acquired B-mode images) to provide $\overline{P_{meas}}$. Then, the T20 blood was removed and the S20 sample was introduced in the Couette device to repeat the same operation at a shear rate of 100 s$^{-1}$.

This reference power spectrum allowed the average power spectrum $\overline{P_{meas}}$ to be normalized. Indeed, the measured backscatter coefficient reported was computed as:

$$BSC_{meas}(k) = BSC_{ref}(k) \frac{\overline{P_{meas}(k)}}{\overline{P_{ref}(k)}}. \quad (7)$$

In equation 7, the backscatter coefficient of this reference sample $BSC_{ref}$ was estimated by using the expression of the Perkus-Yevick packing factor for non-aggregating spheres. The reference sample was used to compensate the backscattered power spectrum $\overline{P_{meas}}$ for the electromechanical system response, and the depth-dependent diffraction and focusing effects caused by the US beam.

Minimization Routine and Results from the Monodisperse Model

By assuming that the RBC radius a and the acoustical properties of plasma and RBCs are known a priori, the unknowns parameters are the radius of aggregates $r_{ag}$ and the internal hematocrit $\phi_i$. The unknown parameters were estimated by matching the measured BSC with the theoretical $BSC_{eq}$ given by equation 2. For this purpose, values of $r_{ag}/a$ and $\phi_i$ were searched as being variables without dimension, minimizing the cost function:

$$FC(r_{ag}/a, \phi_i) = \sum_j \frac{\|BSC_{meas}(k_j) - BSC_{eq}(k_j)\|^2}{\|BSC_{meas}(k_j)\|^2} \quad (8)$$

or a cost function with a weight M for low frequencies inferior to 15 MHz:

$$FC_{LF}(r_{ag}/a, \phi_i) = M \sum_j^{f \le 15MHz} \frac{\|BSC_{meas}(k_j) - BSC_{eq}(k_j)\|^2}{\|BSC_{meas}(k_j)\|^2} + \sum_l^{f > 15 MHz} \frac{\|BSC_{meas}(k_l) - BSC_{eq}(k_l)\|^2}{\|BSC_{meas}(k_l)\|^2} \quad (9)$$

The cost function synthesizes all the wavenumbers within the frequency bandwidth from 8 MHz to 32 MHz, for this example. The solution $(r^*_{ag}(\phi)/a, \phi^*_i(\phi))$ was found by an exhaustive search by computing several values of $BSC_{eq}$ for effective particles of varying radius $r_{ag}/a$ and of varying area fraction $\phi_{ag}$. Herein, $r_{ag}/a$ varied from 1 to 10 with a step of 0.1 and $\phi_i$ varied from 0.65 to 0.9.

Another way to determine experimentally the structural parameters obtained with the EMTSFM model is to use a minimization routine. In this case, it may be useful to calculate the structure factor $S_{ag}$ in equation 2 using an analytical expression of the structure factor for a random distribution of hard-spheres or sticky-hard spheres as established by Wertheim (M. S. Wertheim, "Exact solution of the Percus-Yevick integral equation for hard spheres", Physical Review Letters, vol. 10, no. 8, pp. 321-323, 1963) or Baxter (R. J. Baxter, "Percus-Yevick Equation for Hard Spheres with Surface Adhesion", J. Chem. Phys., vol. 49, pp. 2770-2774, 1968, respectively.

Figure 5:
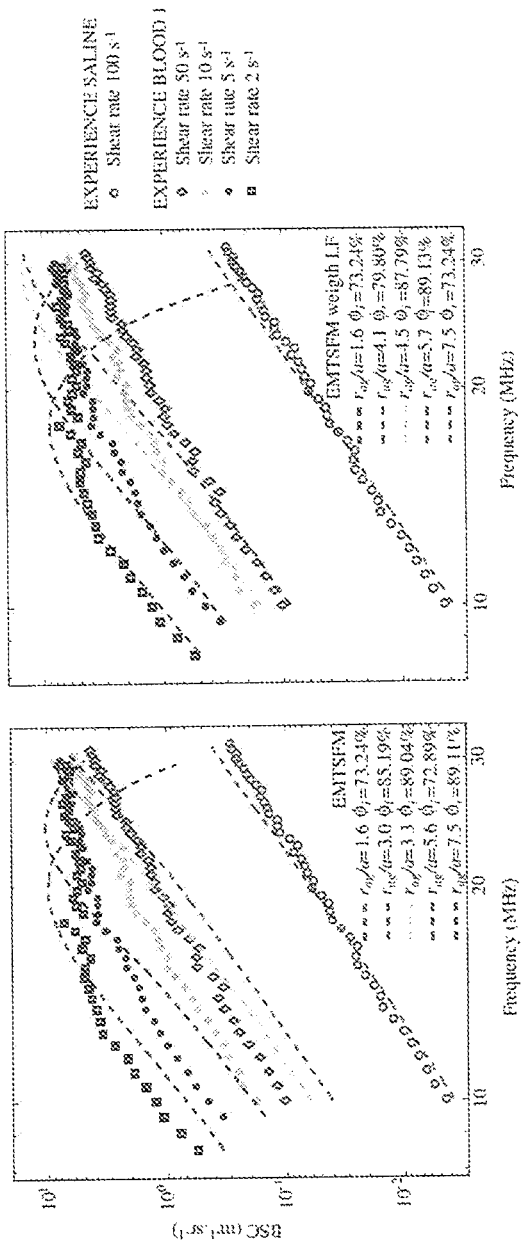
FIG. 5 is a graph of backscatter coefficients for blood sheared at different residual shear rates, and corresponding fitting with the proposed method for monodisperse model (dashed lines)

FIG. 5 shows the typical $BSC_{meas}$ as a function of frequency for different shear rates. The shear rate wa modified in this experimental validation with a Couette flow device to simulate real flows in arteries and veins where the shear rate varies spatially within the vessel. Also represented are corresponding fitted curves obtained with the EMTSFM using a minimization routine with and without putting a weight for the frequencies inferior to 15 MHz (equations 8 and 9). It can be noticed that the $BSC_{meas}$ amplitude as well as the estimation of the aggregate radius $r_{ag}/a$ decrease when the shear rate increases (i.e., when the level of aggregation becomes smaller). On the other hand for this experimental validation, the estimated internal hematocrit did not vary considerably taking values between 0.72 and 0.89. It means that the RBCs within aggregates were densely packed in this experience for all shear rates.

The fitted curves using the cost function with a weight on low frequencies provided a better fit of the $BSC_{meas}$ at low frequencies, as it was expected. Note that the aggregate radii estimated in both cases (with and without weight in the cost function) have similar values. The largest difference in $r_{ag}/a$ is for the shear rate 10 s$^{-1}$. However, in both cases, there was some disagreement between fitted curves and measured BSC data. Another embodiment of the present invention that would consider the polydispersity within the framework of the EMTSFM invention (i.e., a mixture of disaggregated RBCs and identical aggregates of RBCs as modeled in equation 5) would improve the quality of the fits.

Minimization Routine and Results from the Polydisperse Model

The same experimental data of paragraphs 62 to 67 were used the test results of the EMTSFM imaging method if one considers polydisperse structures. By assuming that the RBC radius a and the acoustical properties of plasma and RBCs are known a priori, the unknowns parameters are the radius of aggregates $r_{ag}$, the internal hematocrit $\phi_i$ and the fraction of aggregated RBCs $\Phi$. The unknowns parameters were estimated by matching the measured BSC with the theoretical $BSC_{eqP}$ given by equation 5. For this purpose, values of $r_{ag}/a$, $\phi_i$ and $\Phi$ were searched as being variables without dimension, minimizing the cost function:

$$FC(r_{ag}/a, \phi_i, \Phi) = \sum_j \frac{\|BSC_{meas}(k_j) - BSC_{eqP}(k_j)\|^2}{\|BSC_{meas}(k_j)\|^2} \quad (10)$$

The cost function synthesizes all the wavenumbers within the frequency bandwidth from 8 MHz to 32 MHz, for this example. For a fixed value of $\phi$, the minimum of $FC(r_{ag}/a, \phi_i, \phi)$ occurs at $(r^*_{ag}(\phi)/a, \phi^*_i(\phi))$. The solution $(r^*_{ag}(\phi)/a, \phi^*_i(\phi))$ was found by an exhaustive search by computing several values of $BSC_{eqP}$ for varying values of $r_{ag}/a$, $\phi_i$ and $\phi$. Herein, $r_{ag}/a$ varied from 1 to 10 with a step of 0.1, $\phi_i$ varied from 0.65 to 0.9, and $\Phi$ varied from 0 to 1 with a step of 0.05.

Figure 6:
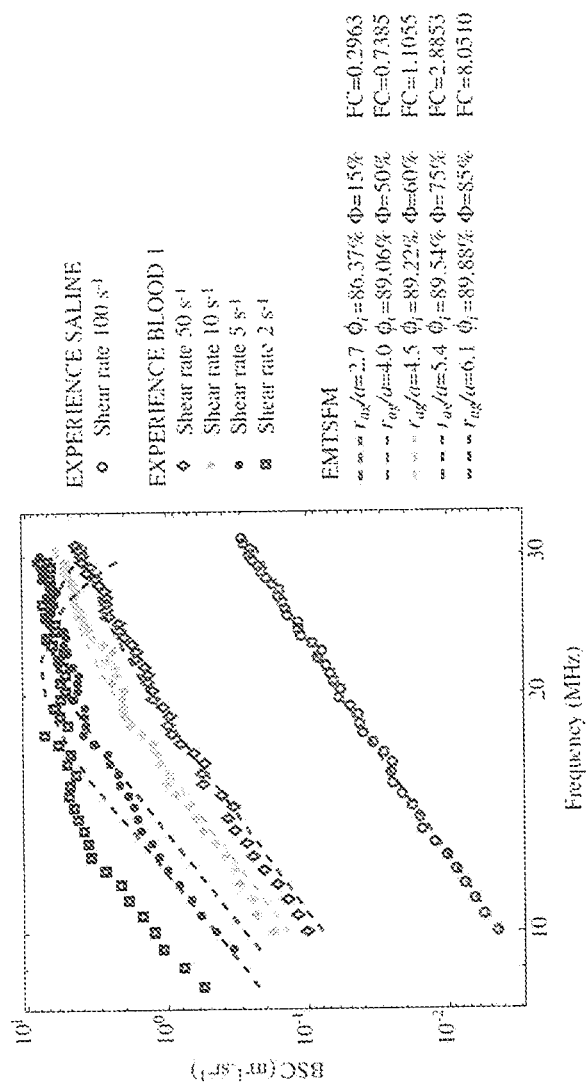
FIG. 6 is the backscatter coefficients for blood sheared at different residual shear rates, and corresponding fitting with the proposed method for polydisperse model considering one size of aggregate and disaggregated RBCs (dashed lines)

FIG. 6 shows the corresponding fitted curves obtained with the proposed EMTSFM method in the case of a polydisperse theory. For each shear rate, the estimated values $r^*_{ag}/a$, $\phi^*_i$ and $\Phi^*$ are given, as well as the values of the cost function $FC(r^*_{ag}/a, \phi^*_i, \Phi^*)$. It can be noticed that the $BSC_{meas}$ amplitude, as well as the estimation of the aggregate radius $r_{ag}/a$ and the fraction of aggregated RBCs $\Phi$, decrease when the shear rate increases (i.e., when the level of aggregation becomes smaller). In the case of this model, the internal hematocrit again did not vary significantly, taking values between 0.86 and 0.89. This seems to reflect a characteristic compactness of porcine blood under shear rate.

By comparing the estimated radius and internal hematocrit estimated by the monodisperse and polydisperse theories, one can notice that the estimated values are quite close. The polydisperse computation using the proposed method (i.e., via the parameter $\Phi$ describing the fraction of aggregated RBCs) fitted very well the experimental BSC curves for the S20 sample and the T20 sample at shear rates of 10 and 50 s$^{-1}$, with low values of the cost function $FC(r^*_{ag}/a, \phi^*_i, \Phi^*) \le 1.1$.

Figure 7:
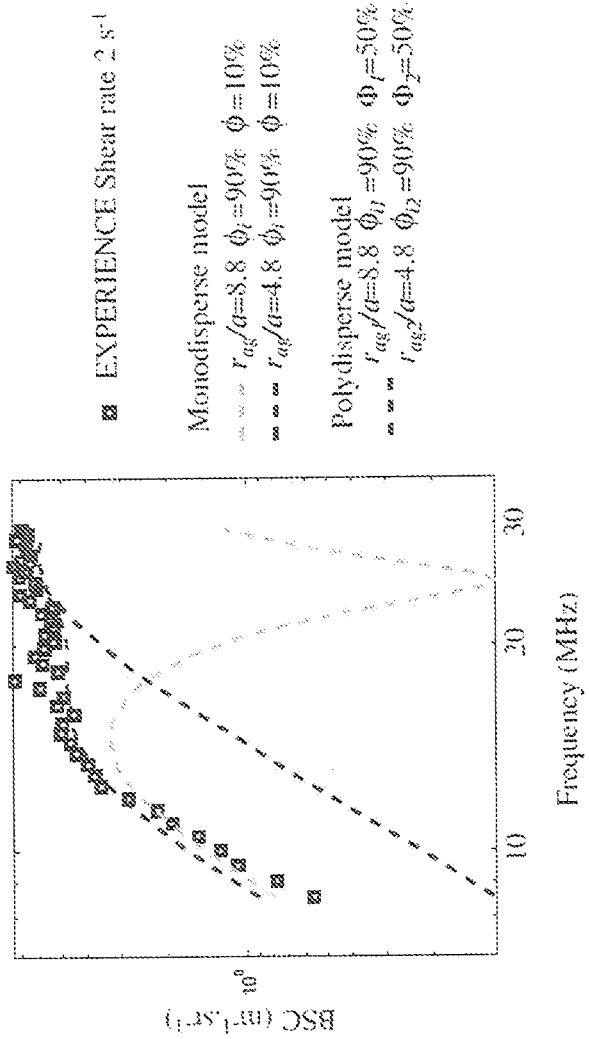
FIG. 7 is a graph representing the backscatter coefficient for blood sheared $2\ s^{-1}$ and the dashed lines the $BSC_{eq}$ computation with the proposed method for polydisperse model (forward problem) considering two sizes of aggregate (dashed lines)
Figure 8:
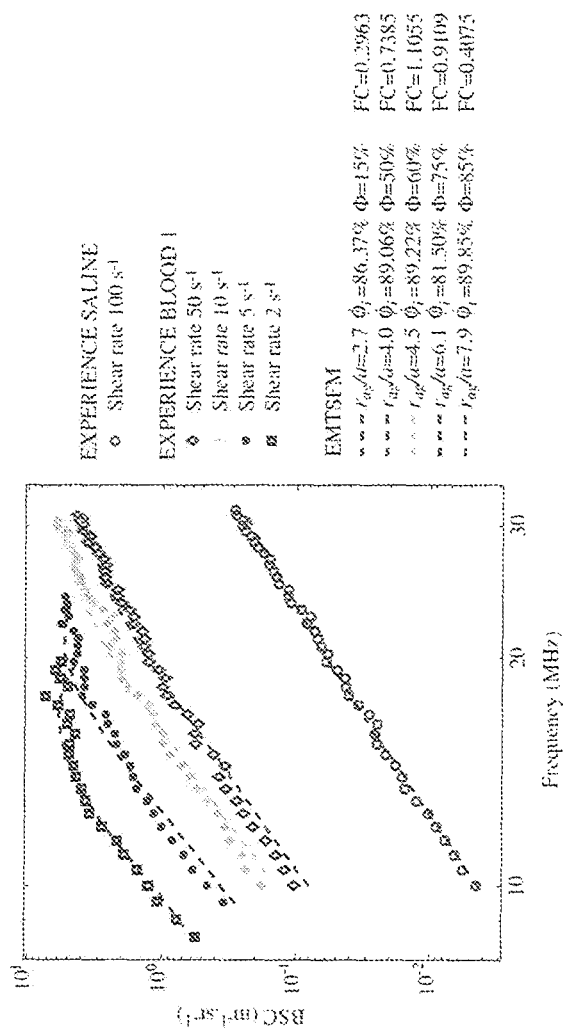
FIG. 8 is the backscatter coefficients for blood sheared at different residual shear rates and corresponding fitting with the proposed method for polydisperse model considering one size of aggregate and disaggregated RBCs (dashed lines).

However, the values of cost function $FC(r^*_{ag}/a, \phi^*_i, \Phi^*)$ are larger for the smallest shear rates 2 and 5 s$^{-1}$ (i.e., the largest level of aggregation). Indeed, there was some disagreement between fitted curves and measured BSC data for these smallest shear rates 2 and 5 s$^{-1}$ in FIG. 6. These bad fits may be due to the presence of several aggregate sizes, whereas the polydisperse model only takes into account one aggregate size with disaggregated RBCs. If you take for example the $BSC_{meas}$ at the shear rate 2 s$^{-1}$, one can observe two peaks as if two aggregate sizes were in the medium. As an example, two backscatter coefficients in black and green were plotted in FIG. 7 corresponding to the computation of the $BSC_{eq}$ with the monodisperse proposed method with two aggregate sizes of $r_{ag1}/a=8.8$ and $r_{ag2}/a=4.8$ for a systemic hematocrit of 10%. If we assume that a fraction of RBCs $\Phi_1$ are aggregated with an aggregate size of radius $r_{ag1}$, while the rest [i.e., a fraction $\Phi_2=(1-\Phi_1)$] are aggregated with an aggregate size of radius $r_{ag2}$, one can compute an equivalent BSC for two sizes of aggregates with a similar mixing law as performed in equation 5. An example of a backscatter coefficient computed with two aggregate sizes is given in blue dashed line in FIG. 7 that fitted very well the measured BSC data. Nevertheless, by considering several aggregate sizes, the theoretical model is improved but larger number of unknowns have to be estimated. Another possibility is to reduce the frequency bandwidth and keep the model presented for equation 5 as shown in FIG. 8. In that case, low values of the cost function $FC(r^*_{ag}/a, \phi^*_i, \Phi^*) \le 1.1$ were obtained for all shear rates, even for the smallest shear rates 2 and 5 s$^{-1}$. But only the largest aggregate size could be estimated.

Discussion of potential impacts of the EMTSFM imaging method

A potential application of the system 10 and method of the present disclosure is the rapid diagnosis of patients with internal organ bleeding, or the evaluation of soldiers on the battlefield. A portable ultrasound device allowing measuring the hematocrit without blood puncture and centrifugation would be highly beneficial. Robust portable ultrasound devices for emergency care or battlefield diagnosis already exist (e.g., Sonosite that was created from financial support of the U.S.A. Army). Adding the possibility of measuring the hematocrit on those scanners would allow the rapid detection of internal organ bleeding (a condition promoting a significant reduction of the hematocrit, i.e., anemia).

RBC aggregation measurements can also be valuable in assessing the response to therapy and changes in the pathological state of many chronic inflammatory diseases that are difficult to monitor clinically. This is particularly true of rheumatoid arthritis, polymyalgia, giant cell arthritis, inflammatory bowel disease, systemic vasculitis, chronic migraine, and genetic blood diseases as beta-thalassemia and sickle-cell anemia. Bacterial infection is the most potent activator of acute inflammation. A high level of RBC aggregation may be a useful indication of intercurrent sepsis, particularly where the kinetics of the acute phase response are known following, for example, major surgeries or organ transplant where there is a risk of silent but serious sepsis. Viral infections cause fewer acute phase responses and the RBC aggregation measurement may be useful in indicating bacterial aetiology in meningitis, neonatal illness and pneumonia. Monitoring RBC aggregate levels could also become a useful indication of response to antibacterial therapy. To add to this broad scope of pathological states where inflammation monitoring is relevant, it should be mentioned that various studies have shown a correlation between inflammation [through high C-reactive protein (CRP) concentration in blood] and future coronary events in patients with unstable angina. Similarly, high inflammation (detected through high levels of CRP) about 6 hours after coronary occlusion is associated with a high mortality or a second infarction in the following 24 hours.

To summarize, inflammation and RBC aggregation are related to numerous diseases and pathological states. There are several million people affected by inflammatory problems, where persistent elevation of RBC aggregation indicates a poor prognosis in both chronic and malignant diseases. For one specific relevant problem like severe sepsis, there are approximately 750,000 cases per year in U.S.A. Furthermore, in those inflammatory conditions, severe RBC aggregation could lead to an acute vaso-occlusive crisis (as in sickle-cell anemia, for example) or thrombotic complications that may be fatal. RBC aggregation has long been recognized as a promoter of vascular thrombosis. Thus, another category of patient that would benefit of such a technology is those at risk of developing deep-vein thrombosis (e.g., hospitalized immobile patients). Deep-vein thrombosis is a condition that can lead to a pulmonary embolism, which is an often fatal event encountered when a vein clot, usually located above the knee, detaches from the vessel wall and migrates up to the pulmonary circulation. Hospitalized patients would benefit from having a constant monitoring of the state of RBC aggregation.

Medical imaging equipment is a key component of the broader family of diagnostic health-care systems. Their primary function is to provide a physical measurement or indication of a patient's medical condition and to assist medical professionals in determining whether further therapy is necessary and what the best course of action is. Among all imaging technologies, ultrasound boasts an extensive array of applications, ranging from foetal heart monitoring to general-purpose abdominal scanning and blood flow imaging. Also, compared to alternative imaging technologies, ultrasound procedures are safe, painless, quick, involve no ionizing radiation, and are highly cost-effective. The method of the present disclosure allows the measurement of the size of RBC aggregates, compactness of aggregates and hematocrit, and could be easily integrated into existing echographic clinical scanners.

The main advantage of the method of the present disclosure in comparison to other approaches used to evaluate the state of inflammation resides in its real-time monitoring capability. The real-time capability is also of high importance for the non-invasive assessment of the hematocrit in critical-care units or battlefields. Other important benefits are:

1) Non-invasiveness: The method of the present disclosure allows measurement of RBC aggregation in vivo, when red blood cell clusters are moving in a vessel. All other methods of inflammation evaluation require withdrawal of blood from the patient. This is an obvious drawback, since there are health and safety issues for both the patient and the person taking the blood sample. More importantly, the method of the present disclosure does not need the use of anticoagulant and the measure is performed in its natural environment. This is a major issue because it is well documented that in vitro assessments of RBC aggregation in a laboratory instrument are affected by the time lapse between blood sampling and measurement, which can be of several hours.

The non-invasive evaluation of the hematocrit without blood withdrawal is also a major advantage for critical-care rapid decisions in hospital and elsewhere.

2) Point-of-care testing: Real-time monitoring of RBC aggregation could be performed, for example, in an emergency or intensive care units with patients in septic shock or at risk of developing septic shock (e.g., after a surgery, HIV-infected patients, graft patients, immuno-depressed patients, patients with cancer or undergoing chemotherapy/radiotherapy, patients who have had an organ transplant). Performing tests at the point of care allows medical practitioners to immediately diagnose and treat patients. Studies have shown that the rapid turnaround time improves patient outcomes, prevents inefficiencies in administrative follow-ups, and minimizes delays in treatments that could otherwise result in adverse complications and costly consequences. The same rationale applies to medical decisions in the battlefield.

3) Monitoring of recovery: Recovery of normal blood circulation during intensive care can be monitored.

4) Self-monitoring of chronic inflammatory diseases: In the same way as monitoring and controlling blood sugar levels play a key role in diagnostic and management of diabetes, the monitoring of RBC aggregation could play a major role in the management of circulatory related disorders like sickle-cell anemia and beta-thalassemia. Individuals with these chronic conditions are usually healthy, but their entire lives are periodically punctuated by painful attacks. Since it is possible to treat a crisis by way of analgesic, hyperhydration or blood transfusion, an early prediction of a crisis through daily monitoring of RBC aggregation would dramatically increase their quality of life.

The scope of the claims should not be limited by the preferred embodiments set forth in the examples, but should be given as the broadest interpretation consistent with the description as a whole.

The invention claimed is:

1. A method for characterizing ultrasound scatterers in a medium, the method comprising:
receiving ultrasound data by an ultrasound receiver of a system for characterizing ultrasound scatterers representing a region of interest comprising a plurality of scatterers in a medium, the plurality of scatterers including aggregates of the scatterers;
modelling the ultrasound data by a processor of the system for characterizing ultrasound scatterers using an effective medium theory combined with the structure factor model, the structure factor model defining the spatial organization and concentration of the aggregates;
comparing the modeled ultrasound data to theoretical data obtained with the effective medium theory combined with the structure factor model; and
determining from the comparison dimensional data of the aggregates of the scatterers and the volume concentration of scatterers in the medium.

2. A method according to claim 1, wherein the modeling includes consideration of aggregated and disaggregated scatterers in the medium, the method further comprising estimating the fraction of aggregated scatterers at the same time as estimating the dimensional data of the aggregates of the scatterers, the volume concentration of scatterers within aggregates and the volume concentration of scatterers in the medium.

3. A system for characterizing ultrasound scatterers in a medium, the system comprising:

a transmitter for transmitting an ultrasound signal to a region of interest, the region of interest comprising a plurality of scatterers in a medium including aggregates of the scatterers;

at least one detector for detecting a scattered or a backscattered ultrasound signal; and a processor for converting the detected ultrasound signal to ultrasound data representing the region of interest, for modeling the ultrasound data using an effective medium theory combined with the structure factor model, the structure factor model defining the spatial organization and concentration of the aggregates; comparing the modeled ultrasound data to theoretical data obtained with the effective medium theory combined with the structure factor model; and determining from the comparison dimensional data of the aggregates of the scatterers and the volume concentration of scatterers in the medium.

* * * * *